(12) United States Patent
Borden

(10) Patent No.: US 9,724,043 B2
(45) Date of Patent: Aug. 8, 2017

(54) SOLID STATE DIODE APPLICATOR DISC

(71) Applicant: Carla Borden, Jonesboro, AR (US)

(72) Inventor: Carla Borden, Jonesboro, AR (US)

(*) Notice: Subject to any disclaimer, the term of this patent is extended or adjusted under 35 U.S.C. 154(b) by 605 days.

(21) Appl. No.: 14/181,961

(22) Filed: Feb. 17, 2014

(65) Prior Publication Data

US 2014/0235992 A1 Aug. 21, 2014

Related U.S. Application Data

(60) Provisional application No. 61/765,251, filed on Feb. 15, 2013.

(51) Int. Cl.
*A61B 5/00* (2006.01)
*A61N 5/10* (2006.01)

(52) U.S. Cl.
CPC .......... *A61B 5/6832* (2013.01); *A61N 5/1071* (2013.01); *A61B 2505/05* (2013.01)

(58) Field of Classification Search
None
See application file for complete search history.

(56) References Cited

U.S. PATENT DOCUMENTS

| | | | |
|---|---|---|---|
| 4,051,842 A | 10/1977 | Hazel | |
| 4,332,257 A | 6/1982 | Ayer | |
| 5,090,410 A | 2/1992 | Saper | |
| 6,169,915 B1 | 1/2001 | Krumbiegel | |
| 6,295,463 B1 | 9/2001 | Stenzler | |
| 6,748,254 B2 | 6/2004 | O'Neil | |
| 6,839,585 B2 | 1/2005 | Lowery | |
| 8,190,229 B2 | 5/2012 | Lowery | |
| 8,452,364 B2 | 5/2013 | Hannula | |
| 8,480,684 B2 | 7/2013 | Bendre | |

*Primary Examiner* — Brian T Gedeon
(74) *Attorney, Agent, or Firm* — Debra K. Winters

(57) ABSTRACT

Provided is a device and method for adhering a solid state diode onto a patient and allowing for monitoring during radiation treatment. More particularly, a diode is placed onto a patient. The diode applicator disc is placed on top of the diode with the center of the diode in the transparent area of the applicator disc. The radiation therapist can verify that the diode is held on the point of interest before the applicator disc is applied to secure the diode to the patient's skin. The transparent center allows for proper visualization during the radiation treatment, and the diode measurement can be taken in real time. Preferred embodiment comprises a foam layer that surrounds the diode, a central aperture, a transparent area for visualization of the diode, and an adhesive layer for attachment to the patient's skin.

13 Claims, 5 Drawing Sheets

SOLID STATE DIODE APPLICATOR DISC

CROSS-REFERENCE TO RELATED APPLICATIONS

This application claims priority to U.S. Provisional Patent Application No. 61/765,251, filed Feb. 15, 2013, the disclosure of which is herein incorporated by reference in its entirety.

BACKGROUND OF THE INVENTION

The present invention is directed to a simple and economical device for securely holding a solid state diode in place on a patient for the duration of a single radiation treatment and for a method of placement of the device for monitoring measurement readings during the radiation treatment. More particularly, in embodiments, the present invention relates to a novel disposable device that secures placement of the diode directly on the surface of the point of interest target on the patient, allowing for monitoring by continuously visualizing the diode. This device comprises foam tape that surrounds the diode and provides a secure hold for the cable attached to the diode. The adhesive is designed for adherence to the surface of the skin of the patient and to any other solid surface where radiation monitoring is needed. The device further comprises a transparent adhesive center that securely allows for visualization of the diode to ensure accurate placement. The transparent adhesive center is made of material that allows for reliable diode measurement readings, which are essential for accurate dosage in radiation treatment settings.

Over 1.2 million people will receive radiation treatment in the U.S. this year alone. Each of those patients will have a patient treatment dose report that verifies the calculated dose rate to each dose point of interest. Avoiding excessive radiation exposure or misadministration of radiation dose is important in radiation treatment. Additionally, repeatability is important where multiple treatments are common. Each diode must be positioned and repositioned accurately for each radiation therapy treatment to ensure that the proper radiation dose is delivered to the diseased tissue, avoiding the healthy tissue as much as possible. The ideal device preferably will be flexible, allowing it to adhere to curved body surfaces. It also preferably will be capable of use with adults, children, and babies, and for use on various locations of the body.

The use of solid state diodes for monitoring radiation doses to patients during treatment has become the standard in quality assurance. The diode needs to be held in direct contact with the body for a period of time. It often is moved to a different point of interest during the same treatment regime. While the diode is highly technical in the ability to read radiation doses, the ability to securely place it on a patient at a point of interest to monitor the amount of the radiation received has been a problem with which radiation therapists have struggled since the inception of the solid state diode.

The diode itself does not have any properties that allow it to adhere to the patient. Therefore, external mechanisms are used to hold the diode in place. The most common method for holding the diode onto a patient is with conventional tape. This tape is often either made from paper or is masking tape. The use of tape is less than ideal. Many times the tape blocks the ability to see the diode during the treatment so monitoring is less efficient. Additionally, the adhesive on the tape does not provide for adequate adhesion to the curved surface of the body for the duration of the treatment. The tape also leaves an undesirable residue of adhesive both on the diode and on the skin.

Attempts have been made to address these problems for adhering sensors and probes to the patient's body. For example, U.S. Pat. No. 5,090,410 to Saper, incorporated by reference in its entirety herein, describes a fastener for attaching a sensor to the body. The sensor is attached through the use of a sleeve, which in turn is attached to an adhesive bandage. The bandage, while making the sensor more stable to the patient's body, does not provide an adequate structure to hold the diode sufficiently close to the patient's skin. Furthermore, the shape and size of the design of this fastener would not take into account the size of the diode and are therefore not applicable for use with a solid state diode. While U.S. Pat. No. 6,748,254 to O'Neil contains a plurality of stacked adhesive layers with the topmost adhesive layer attached to the patient's skin, the optical sensor of interest is built into the applicator. Such a device would not accommodate the solid state diode because visualization of the target and diode placement would be impossible. Additionally, this device would not hold the diode on the surface of the patient.

U.S. Pat. No. 8,190,229 to Lowery holds a sensor in an interior cavity that can be adhered to the patient's skin. The overall design contains flaws for radiation treatment with the solid state diode because the flanges of the roof portion of the device would prevent visualization of the target and of the diode. This would not allow accurate placement. Additionally, the pressure application portion would prevent the diode from being placed directly on the target. A device such as the one in U.S. Pat. No. 6,295,463 to Stenzler would impede the ability to get an accurate reading because the mount is between the sensor and the target.

Methods and devices intended for radiation treatment such as U.S. Pat. No. 8,480,684 to Bendre are simply positioning devices and not capable of allowing for visualization during treatment. These methods are unreliable in the treatment and do not allow visualization of the target. All above-mentioned patents are incorporated by reference in their entireties.

Problems with the current external mechanisms include: lack of visualization of the target; improper placement of diode; lack of consistent adhesion during monitoring; and lack of consistent adhesion in adjusting the placement of the diode. There is no current technology that meets the specific needs of the diode application and addresses these problems.

From the above discussion, it is apparent that what is desired is a dedicated device to hold the solid state diode onto a patient during dose monitoring and to ensure proper radiation treatment with monitoring in real time during the radiation procedure. The present invention is an effective method for visualizing the target, and it is made of materials that are reliable in adhesion to the skin. It delivers accurate and reliable placement of the monitoring device on the patient and is uniquely designed for use with a solid state diode, thus addressing the problems of the current technology. In addition, there are lower repeat rates of diode readings with the present invention, and the setup time for a diode reading is reduced. Additionally, the present invention is sufficiently sized to use with adults, children, and babies.

Any references mentioned are not admitted to be prior art with respect to the present invention.

SUMMARY OF THE INVENTION

The numerous limitations inherent in the current technology described above provide great incentive for a better device and method both for adhering the solid state diode onto the patient and for allowing for proper real-time monitoring during the treatment. In embodiments, a solid state diode is placed onto a patient at the point of interest. The solid state diode applicator disc is then placed on top of the diode, with the center of the diode in the transparent area of applicator disc. By way of visual inspection through the transparent adhesive center, the radiation therapist can verify that the applicator disc is holding the diode in the correct position on the point of interest before the foam applicator disc is applied to secure the diode. The transparent adhesive center allows for proper visualization during the radiation treatment, and the diode measurement can than be taken in real time. If the diode is initially not placed in the correct location, it can be removed and repositioned on the patient up to four times before a new applicator disc will be employed.

BRIEF DESCRIPTION OF THE DRAWINGS

So that those skilled in the art to which the present invention appertains will readily understand how to make and use the device and method of the present invention without undue experimentation, preferred embodiments thereof will be described in detail herein below with reference to certain figures, wherein.

DETAILED DESCRIPTION OF PREFERRED EMBODIMENTS

Figure 1:
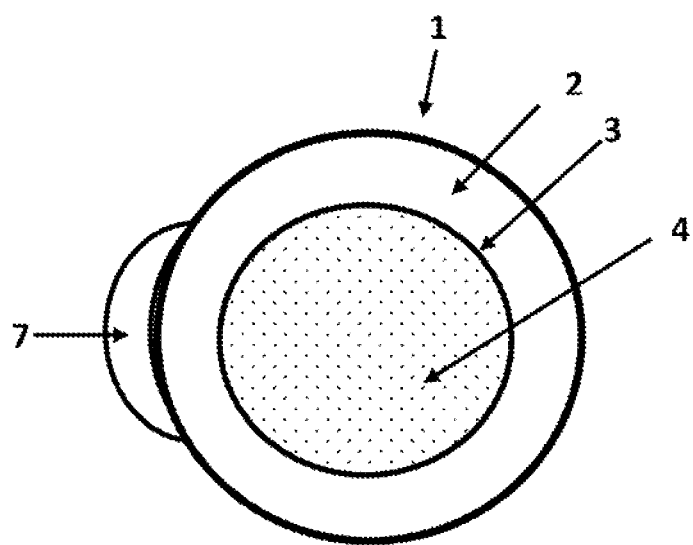
FIG. 1 illustrates a top elevation view according to a preferred embodiment of the applicator disc device.

Reference will now be made in detail to various exemplary embodiments of the invention. Embodiments described in the description and shown in the figures are illustrative only and are not intended to limit the scope of the invention, and changes may be made in the specific embodiments described in this specification and accompanying drawings such that a person of ordinary skill in the art will recognize are within the scope and spirit of the invention.

Disclosed herein are detailed descriptions of specific embodiments of the device and method of the present invention for adhering a solid state diode to a patient for radiation treatment and for real time monitoring during the radiation treatment. It will be understood that the disclosed embodiments are merely examples of ways in which certain aspects of the invention can be implemented and do not represent an exhaustive list of all of the ways the invention may be embodied. Indeed, it will be understood that the devices and methods described herein may be embodied in various and alternative forms.

An object of the present invention is to provide a device that provides secure, proper placement of the solid state diode during radiation treatment. Another object of the present invention is to provide a device that allows for continuous visual inspection of the target during radiation treatment. Yet another object of the present invention is to provide a device that allows for consistent adhesion in adjusting the placement of the diode and during monitoring.

Referring now to the drawings in detail, FIGS. 1-5 show a first embodiment of the present invention where the applicator disc 1, preferably round in shape, holds a solid state diode 6 securely on the surface of the patient's skin 8 by use of an adhesive layer 5 attached to a foam 2 layer and a transparent adhesive film 4 layer. The foam layer 2 is preferably made of material that is optically opaque, while the adhesive film 4 layer is preferably made of material that is transparent and provides for continuous visualization of the diode during the radiation treatment. In addition, the applicator disc 1 is preferably flexible and resilient so that it can curve and conform to differently shaped body surfaces.

FIG. 1 shows an embodiment where the applicator disc 1 has an outer diameter about 2.0 inches and is in the shape of a round ring. The foam layer 2 is preferably made of foam tape with a pull tab 7 on at least one side, and possibly both sides. The pull tab 7 is held by the radiation therapist during the application and removal of the applicator disc 1. The pull tab 7 preferably is made a part of the foam layer 2. The innermost part of the ring-shape device has a circular cutout aperture 3 from about up to 1 inch and preferably includes a transparent adhesive film 4 that is adhesively attached to the aperture 3 of the foam layer 2 of the applicator disc 1. The overall width of the applicator disc 1 is about 0.125 inches.

Figure 2:
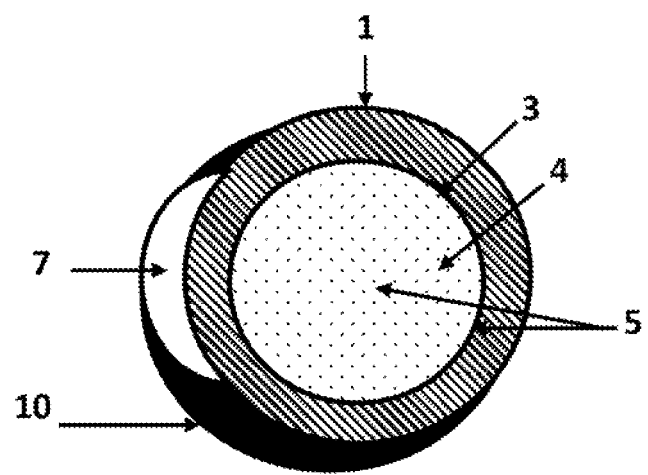
FIG. 2 illustrates a bottom elevation view according to a preferred embodiment of the applicator disc device.
Figure 5:
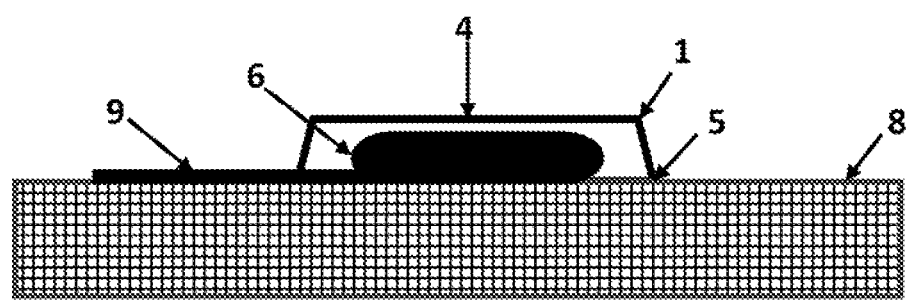
FIG. 5 illustrates a cross section vied according to a preferred embodiment of the applicator disc device as used in conjunction with a diode held on the surface of a patient.

Referring to FIG. 2, a bottom view of an embodiment of the ring-shaped device can be seen. The back of the applicator disc 1 has a synthetic medical grade adhesive layer 5 for attachment to the patient's skin. The adhesive layer 5 has properties that allow for application, removal, and reapplication. The adhesive layer 5 causes no dermal damage when the applicator disc 1 is removed. The adhesive layer 5 is covered with a paper backing 10 that is removable. The transparent adhesive film 4 can be seen through the aperture 3 from the bottom view, as seen in FIG. 2. The pull tab 7 is covered with a paper backing 10 that is removable. The paper backing 10 can be removed so the pull tab 7 adheres to the patient's skin 8 (as seen in FIG. 5). Preferably the paper backing 10 is not removed from the pull tab 7 making removal of the disc 1 from the patient's skin 8 more easily accomplished.

Figure 3:
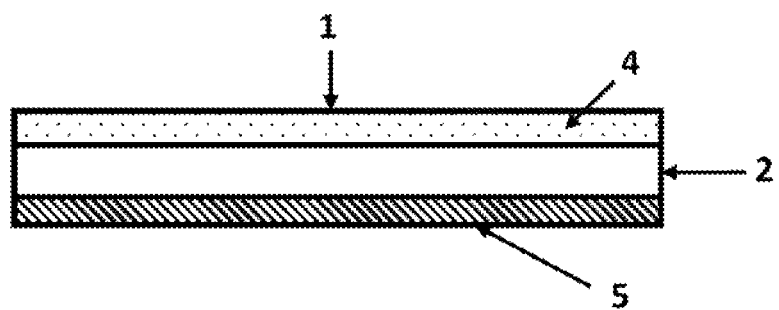
FIG. 3 illustrates a cross-sectional view according to a preferred embodiment of the applicator disc device

As shown in FIG. 3, an embodiment of the applicator disc 1 is attached to the skin by the adhesive layer 5. Preferably, the adhesive layer 5 is applied to the entire lower foam surface layer 2 of the applicator disc 1, but in an alternative embodiment some sections may remain free of adhesive, while the adhesive covers only parts of the lower foam layer 2. The transparent film 4 covers the top of the open innermost part of the circle from about up to ⅛" foam applicator disc 1.

Figure 4:
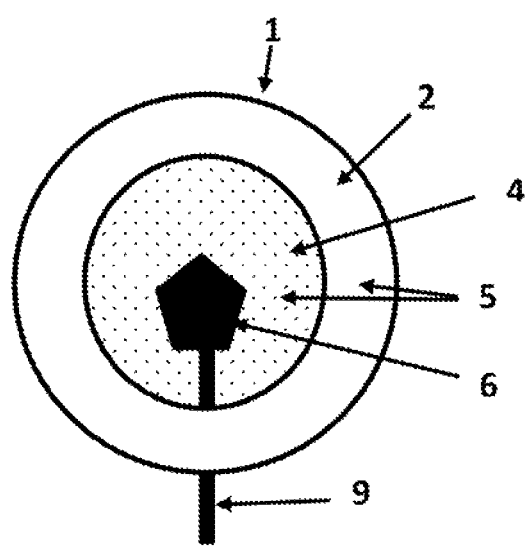
FIG. 4 illustrates a top view according to a preferred embodiment of the applicator disc device with the diode monitor in place.

FIG. 4 shows an embodiment of the applicator disc 1 securing the diode 6 with visualization through the transparent film layer 4. The foam layer 2 can be seen located as the outer ring structure of the applicator disc device 1. The diode 6 is centered below the transparent film 4 on the adhesive layer 6 side of the applicator disc 1. The applicator disc 1 fits over and surrounds the diode 6 placed below it. The diode cable 9 is secured under the adhesive layer 5.

As seen in FIG. 5, the adhesive layer 5 is preferably attached to the skin of the patient 8. The diode cable 9 is securely held by the adhesive layer 5, and continuous visualization is through the transparent film layer 4. The diode cable 9 is covered by the applicator disc 1 and extends under the applicator disc 1 to the electrometer. The diode 6 is connected to the diode cable 9 and is centered under the transparent film 4.

As will be understood by those skilled in the art, the present invention may be embodied in other specific forms without departing from the essential characteristics thereof. For example, the disc may be configured for use on an adult, pediatric, or neonatal patient, or the disc may use other suitable materials other than those described above. These other embodiments are intended to be included within the scope of the present invention, which is set forth in the claims.

In a preferred embodiment the outer diameter of the applicator disc device is from about 1.5 inches to about 2.5 inches, and the inner diameter of the open circle is from about 0.5 inch to about 1 inch. The foam layer preferably is Microfoam™ Medical Tape about 5 mils thick. Preferably, the adhesive attached to the foam is from about 1.5 mils to about 1.75 mils thick. Any skin-friendly, biocompatible, medical-grade adhesive that would not damage the surface of sensitive skin may be used. Preferably the adhesive is of the release type so it can be easily removed.

In various embodiments, the film material could be any flexible medical grade transparent adhesive. In various embodiments, the foam material could be any type of flexible non-toxic radiolucent material impermeable to body fluid that could handle the stress of repetitive attachment and detachment of the applicator disc without failure by tearing or otherwise. The adhesive foam need not be in a defined shape but may be continuous adhesive surfaces. Any shaped foam adhesive that secures a solid state diode onto any object where a radiation reading is needed could be various embodiments.

In various embodiments the foam layer is fabricated from latex-free, hypoallergenic, elastic foam tape designed to stretch and conform while providing secure adhesion to joints and to skin folds. Alternatively, the foam layer is fabricated from other flexible materials that are non-toxic, impermeable to body fluid, and capable of withstanding the stress of repetitive attachment and detachment of the device without failure by tearing or otherwise. Preferably the material would have adhesive on one side.

In various embodiments, the shape of the applicator disc could be square, rectangular, triangle, oval, and any shape that will accommodate the other components of the applicator disc. In various embodiments, the shape of the cut out aperture could be square, rectangular, triangular, oval, or any other shape that could accommodate the film and visualization of the diode.

In various embodiments, the outer size of the applicator disc could vary from about 1.5 inches to about 2 inches, while the inner diameter could vary from about 0.75 inches to about 1 inch.

The method for use involves the radiation therapist holding the applicator disc 1 by the pull tab 7. The applicator disc 1 is situated on top of the diode cable 9 and the diode 6, such that the diode 6 is in the center of the transparent adhesive film 4 circle with the adhesive layer 5 on the bottom of the applicator disc 1. The diode 6 is placed on the point of interest within the target area on the patient's skin 8. The correct position on the point of interest can be verified visually through the transparent adhesive film 4 before the applicator disc 1 is applied. Finger pressure is applied to the point of interest to secure the applicator disc 1. If the diode 6 is not in proper placement, the applicator disc 1 may be removed using the pull tab 7 and repositioned. The applicator disc 1 is secured to the patient's skin by pressing the foam edge of the applicator disc 1 with light pressure to the patient's skin 8.

The applicator disc 1 adheres such that it is not permanently attached. Visualization of the diode 6 on the point of interest is continuous. There is secure placement of the diode 6 during the radiation treatment, allowing for real-time monitoring of the treatment dose. After the initial placement of the applicator disc 1, the disc may be removed and repositioned on the patient at least four times before a new applicator disc 1 is used. Usual radiation treatment involves repositioning twice. At the end of the radiation treatment, the final removal of the diode 6 is easily accomplished using the pull tab 7. The pull tab 7 is pulled upward, and the diode 6 is removed. The disc 1 can be properly disposed of.

While the present invention has been described with respect to a solid state diode, it should be understood that it is equally applicable to other types of sensors where secure placement and monitoring are essential.

One of the many potential advantages of the present invention, only some of which are discussed in this specification, includes that the present invention provides a secure attachment of the solid state diode to the patient for radiation therapy. Another advantage of the present invention is to provide for a way to visualize the placement of the diode so that inaccurate placement rates decrease. Yet another advantage of the present invention is the ease with which the diode can be attached and removed for radiation treatment. Therefore, the present invention can attain the ends and advantages mentioned, as well as those that are inherent therein.

The terms and expressions that have been employed are used as terms of description, and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification, and variation of the concepts herein disclosed may be resorted to by those skilled in the art, and that such modifications and variations are considered to be within the scope of this invention as defined by the appended claims. Thus, additional embodiments are within the scope of the invention and within the claims that follow.

In general, the terms and phrases used herein have their art-recognized meaning, which can be found by reference to standard texts, journal references, and contexts known to those skilled in the art. The preceding definitions are provided to clarify their specific use in the context of the invention.

All patents and publications mentioned in the specification are indicative of the levels of skill of those skilled in the art to which the invention appertains. All references cited herein are hereby incorporated by reference to the extent that there is no inconsistency with the disclosure of this specification.

The figures are not necessarily to scale, and some features may be exaggerated or minimized to show details of particular components. Well-known components, materials, or methods are not necessarily described in great detail so as to avoid obscuring the present disclosure.

Figures illustrating the components show some elements that are known and will be recognized by one skilled in the art. The detailed descriptions of such elements are not necessary to an understanding of the invention, and accordingly, are herein presented only to the degree necessary to facilitate an understanding of the novel features of the present invention.

The present invention has been described with reference to particular embodiments having various features. It will be apparent to those skilled in the art that various modifications and variations can be made in the practice of the present invention without departing from the scoped or spirit of the invention. One skilled in the art will recognize that these features may be used singularly or in any combination based on the requirements and specifications of a given application or design. Other embodiments of the invention will be apparent to those skilled in the art from consideration of the specification and practice of the invention in particular by combining the specified features of one embodiment with one or more features of another embodiment. It is intended that the specification and examples be considered as exemplary in nature and that variations that do not depart from the essence of the invention are intended to be within the scope of the invention.

The present invention may be modified and practiced in different but equivalent manners apparent to those skilled in the art having the benefit of the teachings herein. Furthermore, no limitations are intended to the details of construction or design herein shown. It is therefore evident that the particular illustrative embodiments disclosed above may be altered or modified, and all such variations are considered within the scope and spirit of the present invention.

While embodiments are described in terms of "comprising," "containing," or "including" various components and steps. All numbers and ranges disclosed above may vary by some amount. Whenever a numerical range with a lower limit and an upper limit is disclosed, any number and any included range falling within the range are specifically disclosed. In particular, every range of values (or the form, "from about a to about b" or "from approximately a to b," or "from approximately a-b") disclosed herein is to be understood to set forth every number and range encompassed within the broader range of values. Also, the terms in the claims have their plain, ordinary meaning unless otherwise explicitly defined. Moreover, the indefinite articles, "a" or "an" as used in the claims, are defined herein to mean one, at least one, or more than one of the elements that it introduces.

We claim:

1. A device for attaching a solid state diode securely to a patient's skin for assuring accurate radiation diode placement and monitoring during patient radiation treatment, comprising:
    a) an optically opaque foam layer for attaching to a patient's skin; and
    b) a central aperture in said optically opaque foam layer for receiving a radiation treatment diode; and
    c) a transparent adhesive film layer covering and attached to said optically opaque foam layer with an adhesive so as to cover said central aperture and permit monitoring of the radiation treatment diode during a patient radiation treatment; and
    d) an adhesive layer for attachment to a patient's skin and positioned below and attached to said optically opaque foam layer so as to cover the entire optically opaque foam layer; and
    e) a removable paper backing covering said adhesive layer for being removed and exposing said adhesive layer for attachment to a patient's skin.

2. The device of claim 1, wherein said optically opaque foam layer further comprises a foam tape comprising a pull tab on at least one side.

3. The device of claim 2, wherein said transparent adhesive covers a top innermost portion of said central aperture for continuous visualization of the radiation treatment diode during patient radiation treatment.

4. The device of claim 3, wherein the adhesive layer is made of medical grade adhesive.

5. The device of claim 4, wherein the adhesive layer temporarily adheres to the patient's skin.

6. The device of claim 2, further comprising at least one pull tab that extends radially outward from the foam layer.

7. The device of claim 1, wherein the device is generally round in shape to cover and surround the solid state diode.

8. The device of claim 7, wherein the device is from about 1.50~2 inches in outer diameter.

9. The device of claim 8, wherein the central aperture is from about 0.75~1 inches in diameter.

10. The device of claim 9, wherein the device comprises a curved surface configured to fit the curvature of a patient's body.

11. The device of claim 1, wherein the foam layer is configured so that when the device is positioned over the solid state diode it attaches to the patient's skin by adhesion with the adhesive layer.

12. A method for placing a solid state diode onto a target area of a patient's skin for assuring accurate radiation diode placement during radiation therapy, comprising the steps of:
    a) handling a pull tab, positioning an applicator disc over the radiation treatment diode, said applicator disc comprising:
        an optically opaque foam layer comprising an adhesive foam layer for attaching to a patient's skin; and
        a central aperture in the said optically opaque foam layer for receiving a radiation treatment diode; and
        a transparent adhesive film layer covering and attached to the said optically opaque foam layer with an adhesive so as to cover the said central aperture and permit monitoring of the radiation treatment diode during a patient radiation treatment; and
        an adhesive layer for attachment to a patient's skin and positioned below the layer and attached to said optically opaque foam layer so as to cover the entire optically opaque foam layer; and
        a removable paper backing covering the said adhesive layer for being removed and exposing said adhesive layer for attachment to a patient's skin,
    b) positioning the radiation treatment diode in the central aperture of said transparent adhesive film layer;
    c) placing the radiation treatment diode on the target area of the patient's skin;
    d) removing said removable paper backing covering from said adhesive layer of the applicator disc to expose an adhesive surface;
    e) adhering said applicator disc to the patient's skin with pressure to hold the said applicator disc securely, but not permanently to the patient's skin during the radiation treatment;
    f) removing said applicator disc after radiation therapy by handling the pull tab;
    g) removing the radiation treatment diode from the skin of the patient
    h) disposing of said applicator disc.

13. The method of claim 12, wherein there is continuous visualization of the diode on the point of interest of the patient's skin for monitoring the amount of radiation received.

\* \* \* \* \*